United States Patent
Smith et al.

(10) Patent No.: US 9,989,454 B2
(45) Date of Patent: Jun. 5, 2018

(54) METHOD AND APPARATUS FOR MEASURING PARAMETERS OF OPTICAL ANISOTROPY

(71) Applicant: Axometrics, Inc., Huntsville, AL (US)

(72) Inventors: Matthew H. Smith, Madison, AL (US); Yang Zou, Madison, AL (US)

(73) Assignee: Axometrics, Inc., Huntsville, AL (US)

( * ) Notice: Subject to any disclaimer, the term of this patent is extended or adjusted under 35 U.S.C. 154(b) by 639 days.

(21) Appl. No.: 14/504,426

(22) Filed: Oct. 2, 2014

(65) Prior Publication Data

US 2015/0100277 A1     Apr. 9, 2015

Related U.S. Application Data

(60) Provisional application No. 61/887,163, filed on Oct. 4, 2013.

(51) Int. Cl.
| | | |
|---|---|---|
| *G01N 21/21* | (2006.01) | |
| *G01N 21/23* | (2006.01) | |
| *G01N 21/19* | (2006.01) | |

(52) U.S. Cl.
CPC ............ *G01N 21/21* (2013.01); *G01N 21/19* (2013.01); *G01N 21/23* (2013.01)

(58) Field of Classification Search
CPC ............ G01N 21/21; G01N 21/23; G01J 4/04
See application file for complete search history.

(56) References Cited

U.S. PATENT DOCUMENTS

| | | | |
|---|---|---|---|
| 6,801,312 B1 * | 10/2004 | Tiwald | G01N 21/211 |
| | | | 356/369 |
| 9,851,294 B1 * | 12/2017 | Hofmann | G01N 21/211 |
| 2003/0058442 A1 | 3/2003 | Garab et al. | |
| 2007/0146632 A1 | 6/2007 | Chipman | |

(Continued)

FOREIGN PATENT DOCUMENTS

| | | |
|---|---|---|
| CN | 103134592 A | 6/2013 |
| JP | 2006-226995 | 8/2006 |

(Continued)

OTHER PUBLICATIONS

B. F. Macdonald, et al.—Reflection anisotropy spectroscopy: A probe of rubbed polyimide liquid crystal alignment layers, J. App. Phys. 93(8), 4442-4446 (2003).

(Continued)

*Primary Examiner* — Bryan Bui
(74) *Attorney, Agent, or Firm* — Davidson Berquist Jackson & Gowdey, LLP

(57) ABSTRACT

Methods and systems are provided to measure the optical anisotropy properties of a film on glass or other substrates. This technique is suitable for production environments, and is not strongly affected by the TFT or CF active area on LCD panels, even for very high pixel density displays. A method is provided for measuring a magnitude and orientation of optical anisotropy. These methods and systems include an optical anisotropy measurement apparatus for measuring anisotropic materials in a reflection or transmission configuration. The methods and systems may measure a Mueller matrix, diattentuation orientation, or retardance of a sample at one or more rotation angles to calculate anisotropic magnitude and orientation.

8 Claims, 4 Drawing Sheets

(56) References Cited

U.S. PATENT DOCUMENTS

| | | | | |
|---|---|---|---|---|
| 2008/0291463 | A1* | 11/2008 | Milner | A61B 1/00096 356/491 |
| 2009/0296089 | A1 | 12/2009 | Smith | |
| 2012/0044568 | A1* | 2/2012 | Jeon | G02B 27/26 359/465 |

FOREIGN PATENT DOCUMENTS

| | | |
|---|---|---|
| JP | 2008-544302 | 12/2006 |
| JP | 2008-076324 | 4/2008 |
| JP | 2009-69054 | 4/2009 |
| JP | 2010-33040 | 2/2010 |
| JP | 2012-024142 | 2/2012 |
| JP | 2012-198523 | 10/2012 |
| WO | WO 2005/023703 | 3/2005 |

OTHER PUBLICATIONS

F. Yang, et al.—Optical anisotropy and liquid-crystal alignment properties of rubbed olyimide layers, Liquid Crystals 34(12), 1433-1441 (2007).

F. Yang, et al.—Polarization-conversion guided mode (PCGM) technique for exploring thin anisotropic surface layers, Optics Express 15(18), 11234-11240 (2007).

I. Hirosawa—Method of characterizing rubbed polymide film for liquid crystal display devices using reflection ellipsometry, Jpn. J. Appl. Phys. 35, 5873-5875 (1996).

I. Hirosawa—Relation between molecular orientation and rubbing strength observed by reflection ellpsometry, Jpn. J. Appl. Phys. 36, 5192-5196 (1997).

M. F. Toney, et al.—Near-surface alignment of polymers in rubbed films, Nature 374 (20), 709-711 (1995).

M. H. Smith—Optimization of a dual-rotating-retarder Mueller matrix polarimeter, Applied Optics 41(13), 2488-2493 (2002).

N.A.J.M. van Aerle, et al.—Effect of rubbing on the moledular orientation within polyimide orienting layers of liquid crystal displays, J. Appl. Phys. 74(5), 3111-3120 (1993).

S. Y. Lu, et al.—Interpretation of Mueller matrices based on polar decomposition, J. Opt. Soc. Am. A 13(5), 1106-1113 (1996).

PCT/US2014/059177 International Search—Report & Written Opinion dated Jan. 13, 2015.

JP2010-033040 (machine translation).

JP2012-103222 (machine translation).

JP2012-198523 (machine translation).

KR Appln. No. 10-2016-7007723—OA dated Jun. 21, 2017, with English translation.

EP Appln. No. 14850913.6—Extended EP Search Report dated May 4, 2017.

CN Appln. No. 201480049210.8—Office Action dated Feb. 4, 2017.

JP Appln. 2016-545962—Office Action dated Mar. 14, 2017.

KR Appln. No. 10-2016-7007723—OA dated Jun. 21, 2017.

Azzam, R. M. A.: "Photopolarimetric Measurement of the Mueller Matrix by Fourier Analysis of a Single Detected Signal", Optics Letters, vol. 2, No. 6, Jun. 1, 1978, pp. 148-150, XP055043946, ISSN: 0146-9592, DOI: 10.1364/0L.2.000148.

Chenault, D.B.; Pezzaniti, J.L.; Chipman, R.A.: "Mueller Matrix Algorithms", Proc. SPIE on Polarization Analysis and Measurement, vol. 1746, Jul. 19, 1992, pp. 231-246, XP002686817, San Diego DOI: 10.1117/12.138793.

Chipman, Russell A.: "Advances in Polarization Metrology", Proceedings of SPIE, vol. 5156, Nov. 11, 2003, pp. 43-50, XP055043945, ISSN: 0277-786X, DOI: 10.1117/12.511279.

EP Appln. No. 06 784 669.1—Office Action dated Jun. 12, 2017.

European Supplementary Search Report dated Nov. 30, 2012 in EP Appln. No. 06784669.1.

Hilfiker et al., Generalized spectroscopic ellipsometry and Mueller-matrix study of twisted nematic and super twisted nemaytic liquid crystals, Thin Solid F, Elsevier, Amsterdam, NL. vol. 455-456, May 1, 2004.

Matt Smith: "AxoScanTM System Options and Measurement Solutions", Axometrics Inc., 2004, pp. 1-10, XP002686815, Huntsville, USA. Retrieved from the Internet: URL: http://www.jwc.co.kr/admin/common/upload/maker/Axometrics.AxoScan%20C.

Tang S. T. et al.: "Transmissive Liquid Crystal Cell Parameters Measurement by Spectroscopic Ellipsometry", Journal of Applied Physics, vol. 89, No. 1, Jan. 1, 2001, pp. 80-85, XP012052057, American Institute of Physics, New York, US ISSN: 0021-8979, DOI: 10.1063/1.1332800.

Wolfe, Justin et al.: "High-speed Imaging Polarimeter", Proceedings of Spie on Polarization Science and Remote Sensing, vol. 5225, Dec. 9, 2003, pp. 24-32, XP055043489, ISSN: 0277-786X, DOI: 10.1117/12.504439.

Woollam, John A. et al.: "Application of Spectroscopic Ellipsometry to Characterization of Optical Thin Films", Proceedings of SPIE, vol. 4932, May 28, 2003, pp. 393-404, XP055043183, ISSN: 0277-786X, DOI: 10.1117/12.474854.

* cited by examiner

METHOD AND APPARATUS FOR MEASURING PARAMETERS OF OPTICAL ANISOTROPY

RELATED APPLICATIONS

This application claims priority to U.S. Provisional Application Ser. No. 61/887,163 filed Oct. 4, 2013, which is incorporated by reference herein.

FIELD OF THE INVENTION

The present invention generally relates to a method and apparatus for optical anisotropy measurement. More particularly, the present invention relates to a method and an apparatus for measuring an optically anisotropic polyimide (PI) film, or other polymer thin films, in order to determine the anisotropic magnitude and anisotropy orientation of the film.

BACKGROUND

In the production of a liquid crystal devices, including liquid crystal displays (LCD), a film, such as a polyimide film, is applied to the LCD glass. The film is then made to be anisotropic either by mechanically rubbing the film, or by the relatively newer technique of exposing the film to polarized light. Once the film has been made anisotropic, liquid crystal (LC) molecules will tend to align themselves to the anisotropic axis of the film. Further, the magnitude of the film anisotropy relates to the anchoring energy between the LC molecule and the film, and in the case of rubbed PI, dictates the pre-tilt angle of the LC molecule. The anisotropic magnitude and orientation of the optically anisotropic film in a liquid crystal device are major factors determining the performance of the liquid crystal device, and manufacturers need a means for measuring these parameters.

The optical anisotropy is typically the difference between the ordinary and extraordinary refractive indices, $\Delta n = n_o - n_e$, of the film. Because of this anisotropy, the film will exhibit the polarization property of phase retardation or retardance. For an optical beam passing through an anisotropic material, the phase retardance experienced by the beam is $\delta = \Delta n \times t$, where t is the thickness of the material.

The optical anisotropy can also be the difference between the ordinary and extraordinary extinction coefficients, or imaginary components of the refractive index, $\Delta k = k_o - k_e$. In this case, the anisotropy will exhibit the polarization property of dichroism or diattenuation, where the transmittance, or reflectance, of an optical beam varies depending on the polarization state of the optical beam.

In modern liquid crystal devices, the PI film thickness tends to be on the order of 50 nm-100 nm. For rubbed PI, the anisotropy tends to be around $\Delta n \approx 0.005$. And so the retardance of this rubbed PI film would by on the order of 0.25 nm-0.5 nm. For some types of photo-aligned PI, the anisotropy is considerably larger, perhaps $\Delta n \approx 0.05$. In this case, the largest retardance of the anisotropic film that would be expected is around 5 nm.

Accurately measuring retardance magnitude and retardance orientation for samples with retardance in the range 0.25 nm-5 nm is conventionally difficult without proper equipment, however several commercially available measurement systems (e.g., AxoScan™ from Axometrics Inc. of Huntsville, Ala.) can make this measurement with sufficient accuracy. But a problem with making this measurement is that the glass substrate upon which the PI layer is applied will also exhibit retardance due to small stresses within the glass caused during manufacturing. Although the retardance of the glass is quite small, so is the retardance of the anisotropic PI layer. And it is difficult to separate these two sources of retardance in the measurements. As such, simple measurement techniques that only measure the retardance of a sample in transmission have not proven adequate for this application.

Ellipsometry is an optical technique for measuring the thickness and refractive index of thin films based on measuring how a film changes the polarization state of light when the light is reflected from the surface of the sample. Generalized Ellipsometry (GE) is an extension of standard ellipsometry that allows testing anisotropic samples. The GE method is accurate and precise. However, because this method is time-consuming, it is not always practical to use GE measurement in a production environment. An additional difficulty of the GE method is that it becomes increasingly difficult as a measured sample gains in complexity. If a sample has many layers of thin films, additional wavelengths may be needed. Or if the films of the sample are patterned with features smaller than the measurement optical beam diameter, the GE technique may fail completely. Because of those difficulties, the GE method may not be suitable in cases where PI is deposited on the color filter (CF) glass, or on the thin film transistor (TFT) glass of modern high-resolution LCD displays, thus limiting the GE technique to measurement of PI on test glass.

Other efforts that have been made to characterize anisotropic PI films are described in literature discussed below. These techniques focus primarily on rubbed PI films, since rubbed PI films have been used in liquid crystal display industry for decades. However, these methods should also be applicable to measuring photo-aligned PI films also. These methods are described below.

The orientation and anisotropy of rubbed PI films have been studied by retardance measurement, infrared dichroism measurement, and surface second harmonic-generation (see N. A. J. M. van Aerle, et. al., "Effect of rubbing on the molecular orientation within polyimide orienting layers of liquid crystal displays," J. Appl. Phys. 74(5), 3111-3120 (1993), which is incorporated by reference herein). Retardance from the substrate has to be taken into account in the retardance measurement, the infrared dichroism measurement is not sensitive enough due to a very thin film, and surface second harmonic generation requires a complicated measurement setup. Grazing-incidence X-ray scattering method is capable of studying anisotropic PI films in a more sensitive way (see M. F. Toney, et. al., "Near-surface alignment of polymers in rubbed films," Nature 374(20), 709-711 (1995), which is incorporated by reference herein). Generalized ellipsometry method also has been used to study the magnitude and orientation of anisotropic PI films (see I. Hirosawa, "Method of characterizing rubbed polymide film for liquid crystal display devices using reflection ellipsometry," Jpn. J. Appl. Phys. 35, 5873-5875 (1996); see also I. Hirosawa, "Relation between molecular orientation and rubbing strength observed by reflection ellipsometry," Jpn. J. Appl. Phys. 36, 5192-5196 (1997), which are both incorporated by reference herein). Most recently, a Polarization-Conversion Guided Mode technique has been developed to quantify optical anisotropy as low as $10_{-5}$ for a 10 nm surface layer (see F. Yang, et. al., "Polarization-Conversion Guided Mode (PCGM) technique for exploring thin anisotropic surface layers," Optics Express 15(18), 11234-11240 (2007); see also F. Yang, et. al., "Optical anisotropy and liquid-crystal alignment properties of rubbed polyimide layers," Liquid Crystals 34(12), 1433-1441 (2007), which are both incorporated by reference herein). This method requires a prism coupler and refractive index matching fluid to contact the sample. Reflection anisotropy spectroscopy (B. F. Macdonald, et. al., "Reflection anisotropy spectroscopy: A probe of rubbed polyimide liquid crystal alignment layers," J. Appl. Phys. 93(8), 4442-4446 (2003), which is incorporated by reference herein), a technique used to characterize electronic surface states in semiconductors at normal incidence, can be used to test the anisotropy properties of PI films on glass. Most of the above-mentioned methods are too difficult to implement or have insufficient accuracy for use in a production environment.

Another apparatus for measuring the magnitude and orientation of anisotropy has been described (JP Patent Publication No. 2008-76324 11-304645 JP, which is incorporated by reference herein). This technique uses rotating retarders and a half mirror for making measurements in retro-reflection at normal incidence.

It is known that the anisotropy orientation and the relative anisotropy magnitude of PI film on glass can be measured by illuminating a sample at an oblique angle with light polarized in the s plane (polarized parallel to the plane of incidence), and collecting the reflected beam through a polarizer orientated along the p plane (perpendicular to the plane of incidence), and observing the signal as the sample is rotated about its normal through 360 degrees (see Taiwan Patent 095102013, which is incorporated by reference herein). Applying a curve-fit to this signal vs. rotation data allows the anisotropy orientation and the relative anisotropy magnitude to be measured. The relative anisotropy magnitude refers to some measurement parameter that varies when the actual anisotropy magnitude varies. The relative value might not be well calibrated to real values, however this is adequate for monitoring variations during the production process.

The technique described in Taiwan Patent 095102013, which is incorporated by reference herein, is fast enough for use in production environments, and this technique is currently used in the LCD industry. This technique suffers at least one disadvantage when measurements are made on the active area of an LCD glass. The active area is the area of the glass with the patterned pixels, either the color filter (CF) or thin-film transistor (TFT) area. When measuring the CF or TFT active area, this technique requires that a microscopic measurement beam be focused onto a single pixel, and that the measurement apparatus be rotated precisely around this point so that the measurement beam remains in the center of the pixel being tested. As the pixel density of modern cell phones and tablet displays has increased to 300 pixel per inch and beyond, the requirement that the measurement point remain centered on the pixel during rotation significantly increases the system complexity and price. Accordingly, there is a desire for methods and systems to solve these and other related problems.

SUMMARY

A method is provided in an apparatus for measuring optical anisotropic properties of a material, comprising measuring one of: (1) a Mueller matrix of the material, (2) diattenuation orientation of the material, and (3) retardance magnitude of the material. The method further comprises determining a value proportional to anisotropic magnitude of the material based on the measured one of: (1) the Mueller matrix of the material, (2) the diattenuation orientation of the material, and (3) the retardance magnitude of the material.

A method is provided in an apparatus for measuring optical anisotropic properties of a material, comprising measuring a Mueller matrix of the material at a first angle, and determining the diattenuation orientation of the material based on the measured Mueller matrix at the first angle. The method further comprises rotating the material to a second angle, measuring a Mueller matrix of the material at the second angle, and determining the diattenuation orientation of the material based on the measured Mueller matrix at the second angle. Additionally, the method comprises storing a data set of the determined diattenuation orientations and the first and second angles, curve fitting a formula to the stored data set of determined diattenuation orientations and the first and second angles to determine fitting parameters, and determining anisotropic orientation and a value proportional to anisotropic magnitude of the material using the determined fitting parameters.

An apparatus is provided for measuring optical anisotropic properties of a material, comprising a polarimeter configured to measure a Mueller matrix of the material. The apparatus also comprises a processor configured to determine a value proportional to anisotropic magnitude of the material based on the measured Mueller matrix of the material.

An apparatus is provided for measuring optical anisotropic properties of a material, comprising a polarimeter configured to measure a Mueller matrix of the material at a first angle, and measure a Mueller matrix of the material at the second angle. The apparatus further comprises a rotating fixture configured to rotate the material to a second angle. The apparatus also comprises a processor configured to determine the diattenuation orientation of the material based on the measured Mueller matrix at the first angle, and determine the diattenuation orientation of the material based on the measured Mueller matrix at the second angle. The processor is further configured to store a data set of the determined diattenuation orientations and the first and second angles, curve fit a formula to the stored data set of determined diattenuation orientations and the first and second angles to determine fitting parameters, and determine anisotropic orientation and a value proportional to anisotropic magnitude of the material using the determined fitting parameters.

A method is provided in an apparatus for measuring optical anisotropic properties of a material, comprising measuring a Mueller matrix of the material, and determining a value proportional to anisotropic magnitude of the material based on the measured Mueller matrix of the material.

DETAILED DESCRIPTION

Methods and systems in accordance with the present invention measure the optical anisotropy properties of a film on glass or other substrates. This technique is suitable for production environments, and is not strongly affected by the TFT or CF active area on LCD panels, even for very high pixel density displays. In cases where the conventional systems are able to measure on the active area, method and systems in accordance with the present invention may have significantly reduced cost since they do not require the ultra-precision alignment of the beam onto the glass, thus lowering system costs. A method is provided for measuring a magnitude and orientation of optical anisotropy. These methods and systems include an optical anisotropy measurement apparatus for measuring anisotropic materials in a reflection or transmission configuration. The methods and systems may measure a Mueller matrix, diattentuation orientation or retardance of a sample at one or more rotation angles to calculate anisotropic magnitude and orientation. Methods and system in accordance with the present invention provide optical anisotropy measurement for an anisotropic sample by using an exemplary optical anisotropy measurement apparatus as described below.

An exemplary apparatus in accordance with the present invention may measure diattenuation orientation or retardance (specifically retardance magnitude) at a non-normal incident angle, for example, in reflection or transmission. This diattenutation orientation may be measured at a particular rotation angle, and then again at various other rotation angles. The resulting data may be used to determine the anisotropic properties of the sample.

The above-mentioned diattenuation orientation or retardance may be measured by measuring the full Mueller matrix of the sample at a particular angle using, for example, a Mueller matrix polarimeter and then calculating the diattenuation orientation or retardance from the measured Mueller matrix. As mentioned, this process is repeated at various angles and the data (e.g., the diattenuation orientation and the corresponding angle at which it was measured) collected for each angle.

The resulting data is fit to an empirical formula described below. When the data is applied and fit to the formula, two of the resulting known parameters describe the anisotropic magnitude and orientation of the sample.

An exemplary apparatus is capable of measuring both in transmission and in reflection, either with multiple sets of sensors, or a sensor that can be moved to either side of the glass.

Several polarization parameters have been identified that provide a determination of the anisotropic parameters of the sample, when fit through the formula. These include, for example, diattenuation orientation or the retardance magnitude. When these polarization parameters are measured in various angles for a sample, anisotropic magnitude and orientation may be derived through the formula.

Figure 1:
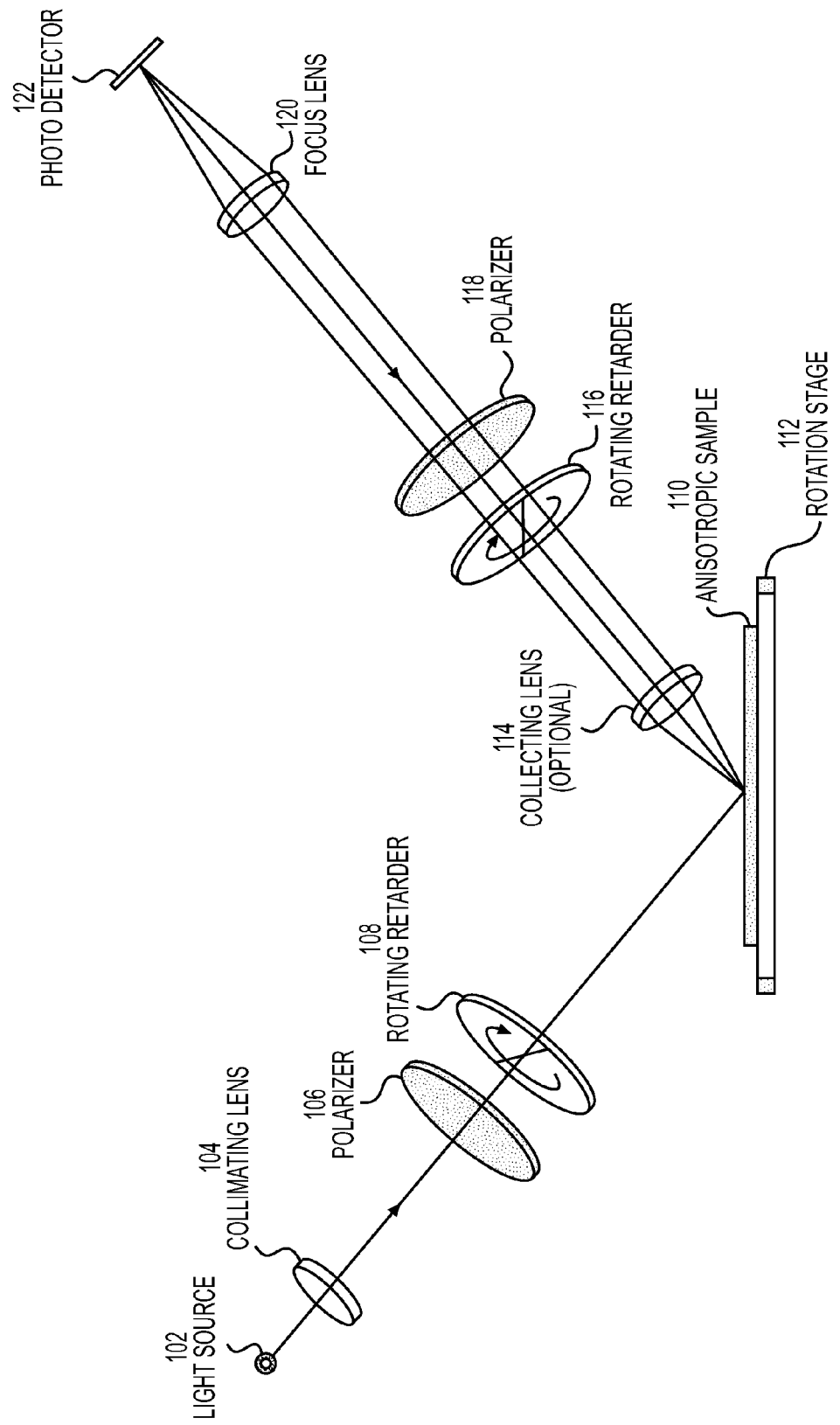
FIG. 1 is a schematic illustration of an exemplary optical anisotropy measurement apparatus in reflection configuration in accordance with methods and systems consistent with the present invention.
Figure 2:
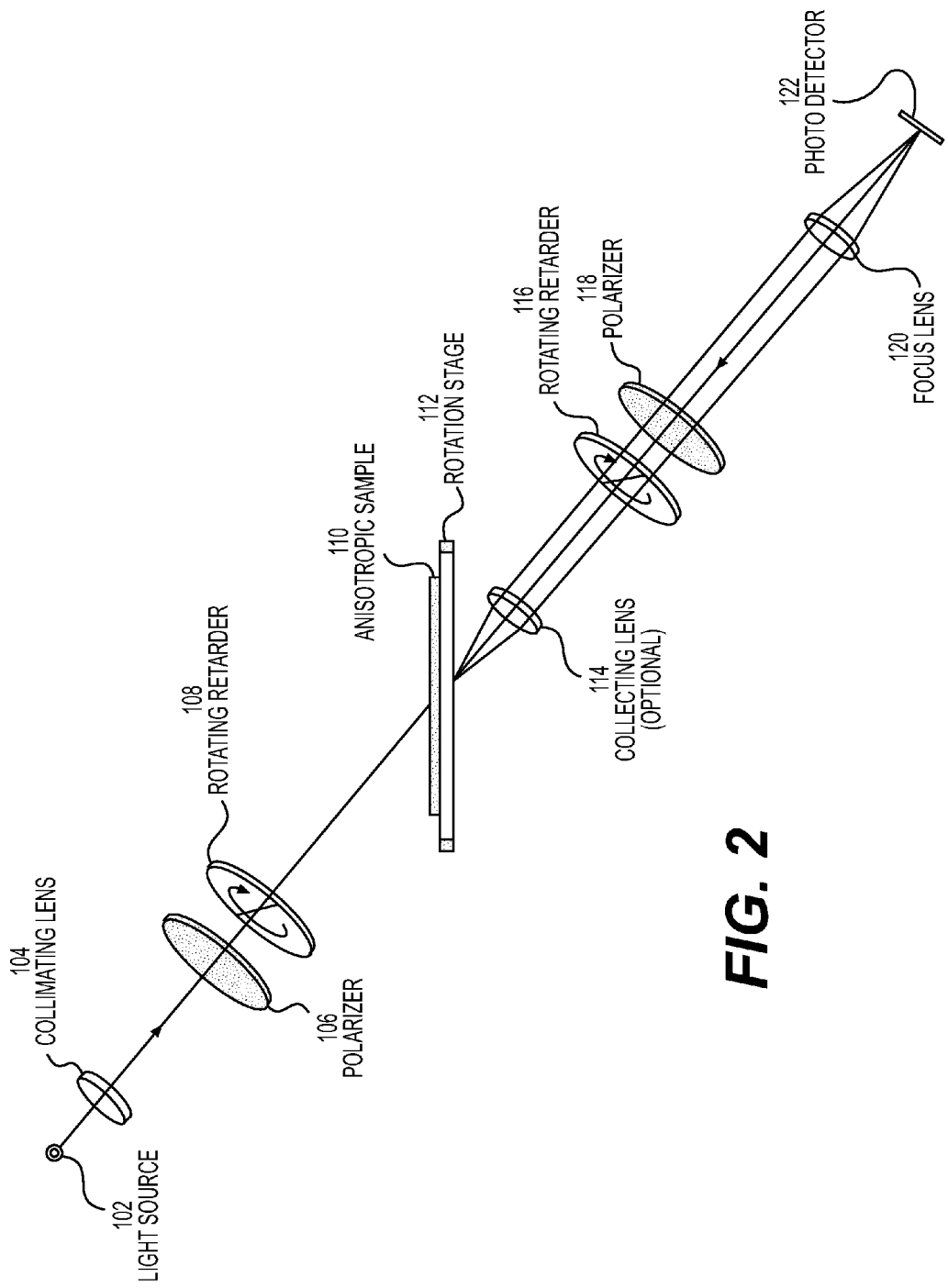
FIG. 2 is a schematic illustration of an exemplary optical anisotropy measurement apparatus in transmission configuration in accordance with methods and systems consistent with the present invention.

FIG. 1 shows an example of the optical anisotropy measurement apparatus in a reflection configuration. In one exemplary implementation, the optical configuration of the apparatus described in FIGS. 1 and 2 is that of a Mueller matrix polarimeter, and the design is fully described in the reference by M. H. Smith, "Optimization of a dual-rotating-retarder Mueller matrix polarimeter," Applied Optics 41(13), 2488-2493 (2002), which is incorporated by reference herein. The Mueller matrix is a 16-element matrix that fully describes the polarization altering properties of a sample. The optical anisotropy measurement apparatus may include a light source 102, collimating lens 104, a polarizer 106, a rotating retarder 108, a rotation stage 112, an optional collecting lens 114, a rotating retarder 116, an analyzer polarizer 118, and a photo detector 122 with focusing lens 120. The rotating retarder is further described in M. H. Smith, "Optimization of a dual-rotating-retarder Mueller matrix polarimeter," Applied Optics 41(13), 2488-2493 (2002). The photo detector 122 may be a photodiode, avalanche photodiode, photomultiplier tube. A sample 110 with optical anisotropy is disposed on the rotation stage 112. The rotation stage 112 rotates with the normal of the sample 110 as rotation axis, when the measurement is performed. In one implementation, the optical apparatus is capable of measuring all polarization parameters, i.e., full Mueller Matrix, at a high speed.

FIG. 2 shows an example of the same optical anisotropy measurement apparatus in a transmission configuration. FIG. 2 shows the same or similar components as FIG. 1, but in a different configuration. In FIGS. 1 and 2, the system is shown with the sample rotating and the sensors fixed. In many cases, especially when the sample becomes large, the sample may be kept stationary while rotating the sensor about an axis normal to the sample. The transmission system in FIG. 2 offers an advantage over the reflection system in FIG. 1 in that the optical alignment and sample flatness are not critical when measuring in transmission. So the anisotropy parameter measurements are not as strongly influenced if the sample is bent or tilted. The reflection system in FIG. 1 offers the advantage that, in addition to measuring the anisotropy parameters from the diattenuation orientation versus rotation angle, the reflection system can also perform generalized ellipsometry measurements.

The diattenuation orientation measured as a function of rotation angle provides excellent determination of the anisotropic properties of a sample. This measurement becomes more accurate at incident angles near the Brewster's angle. This parameter is typically not strongly affected by the presence of the CF or TFT active area, making this measurement suitable for testing high-pixel-density LCD panels. This parameter is typically not strongly affected by the presence of other thin or thick films between the substrate and the anisotropic layer. Optical wavelength and incident angle can be experimentally optimized to reduce the measurement sensitivity these effects. Diattenuation is the polarization property by which the transmittance (or reflectance) of a sample changes for different incident polarization states. Some polarization state will have a maximum transmittance $T_{max}$, and the orthogonal state will necessarily have the minimum transmittance $T_{min}$. The diattenuation magnitude is defined as $D=(T_{max}-T_{max})/(T_{max}+T_{max})$. The diattenuation orientation is the angle of the polarization state corresponding to $T_{max}$. These parameters can be determined from the Mueller matrix.

Figure 3:
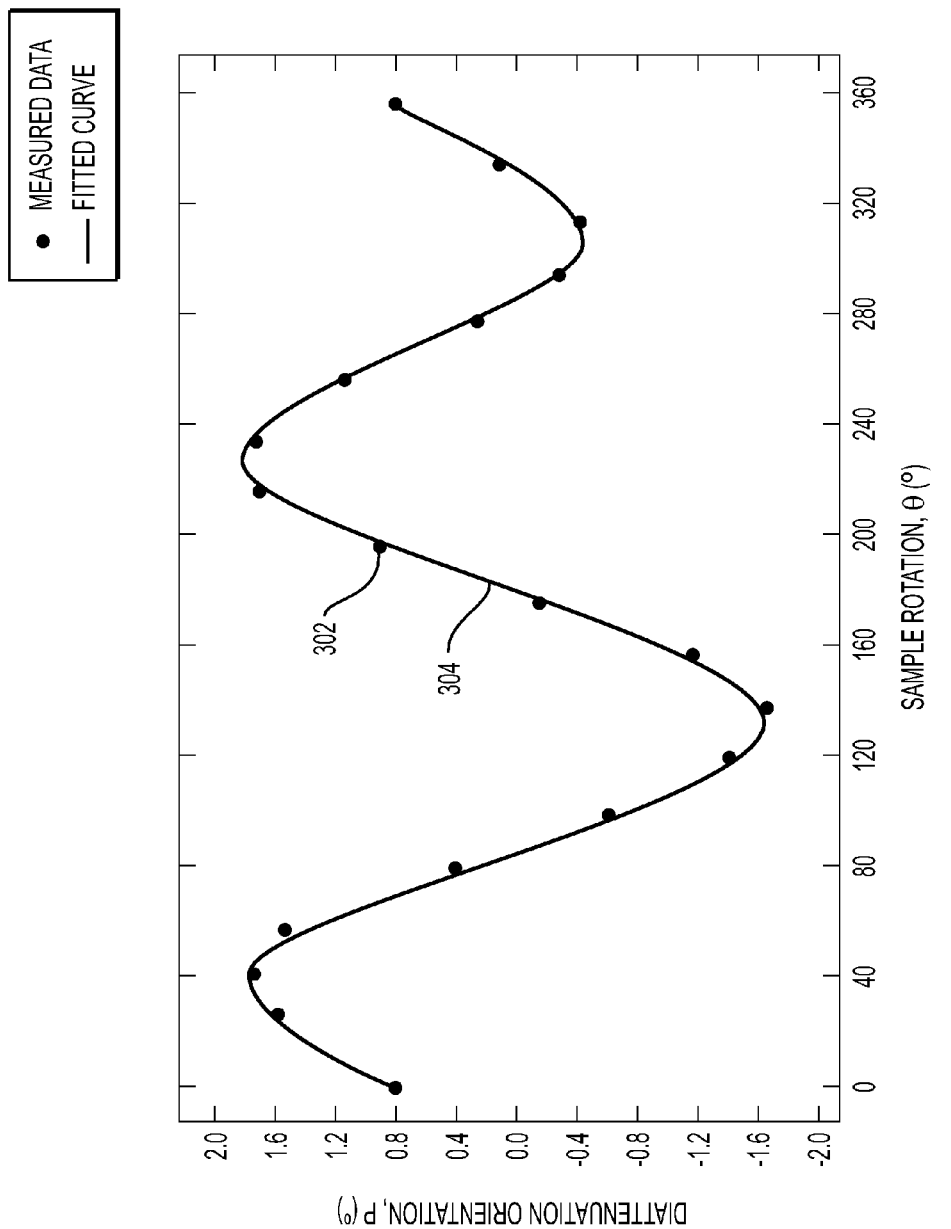
FIG. 3 is a graph showing an example of measured optical anisotropic signal obtained by using the anisotropic measurement apparatus in accordance with methods and systems consistent with the present invention.

FIG. 3 displays a characteristic diattenuation orientation signal as a function of the rotation angle of the sample. The signal shown in FIG. 3 can be used to extract the magnitude and orientation of optical anisotropy of the measured sample. The data points 302 in the FIG. 3 represent a polarization parameter measurement, in this case, diattenuation orientation. This measurement was repeated at sample rotation angles from 0° to 360° in 20° increments. The continuous curve in FIG. 3 represents the best-fit curve 304 as described by Formula 1 below. Other polarization parameters, like retardance magnitude, diattenuation magnitude, etc., can be used to extract the magnitude and orientation of optical anisotropy of the measured sample, too. The method, as described further below, extracts the magnitude and orientation of optical anisotropy and fits the rotational polarization signal, such as diattenuation orientation, retardance magnitude, etc., to an empirical function such as the following function (Formula 1):

$$P = A + B\sin(2\theta + \varphi_B) + C\sin(\theta + \varphi_C)$$

In this function, P is the measured polarization parameter such as diattenuation orientation (and is known from the Mueller matrix measurement of the sample), and θ is the rotation angle of the sample, which is also known.

B is proportional to the anisotropic magnitude of the sample, and $\varphi_B$ is the anisotropy orientation, and are originally unknown before fitting the formula to the data. Since the diattenuation orientation P for many different angles (known θ's) is measured and known, that data and this function may be used to determine B, which is proportional to the anisotropic magnitude, and $\varphi_B$, which is the anisotropy orientation. A non-linear curve fitting algorithm may be applied to the data for P's and corresponding θ's to determine B and $\varphi_B$. Fourier analysis techniques may also be used to make the same determination of B and $\varphi_B$.

Furthermore, depending on the polarization parameter being considered, the other parameters of the empirical function may or may not have any physical meaning. For some parameters, A is proportional to film thickness. For rubbed PI samples, C is proportional to the pre-tilt angle of the PI. The parameter $\varphi_C$ generally does not relate to a physical property of the sample, but instead relates to minor misalignments between the rotation axis of the sample stage and the surface normal (i.e., perpendicular axis) of the sample. Knowing various pairs of P's and θ's (diattenuation orientations and corresponding rotation angles), these parameters may be solved for using non-linear curve fitting and the supplied Formula 1. Other formulas are also possible.

The polarimeter takes the measurements such as the Mueller Matrix, diattenuation orientation and retardance. In one embodiment, a separate fixture connected to the polarimeter rotates the polarimater relative to the sample, or the sample relative to the polarimeter. Both the polarimeter and the rotating fixture may be controlled by a supervisory computer. The various measured parameters such as diattenuation orientation, Mueller matrices, retardance and rotational angles may be stored on the computer, and the calculations including curve fitting may be performed by the computer. The computer may include software and/or hardware such as a processor for implementing the control of the polarimeter, fixture and calculations and any other suitable component or function. The processor may also store the data in a memory on the computer.

In FIGS. 1 and 2, a system is shown capable of measuring the full Mueller matrix of the sample. However, for the purposes of measuring diattenuation orientation, it is not necessary to measure the full Mueller matrix. Less complex measurement systems that can only measure the diattenuation orientation would also provide the data needed for the empirical Formula 1 shown above to determine the anisotropy parameters. The most simple design of such a system would be a light source followed by a rotating polarizer used to illuminate the sample, and a polarization-insensitive detector (such as an integrating sphere and photodiode) to collect the reflected or transmitted beam.

Figure 4:
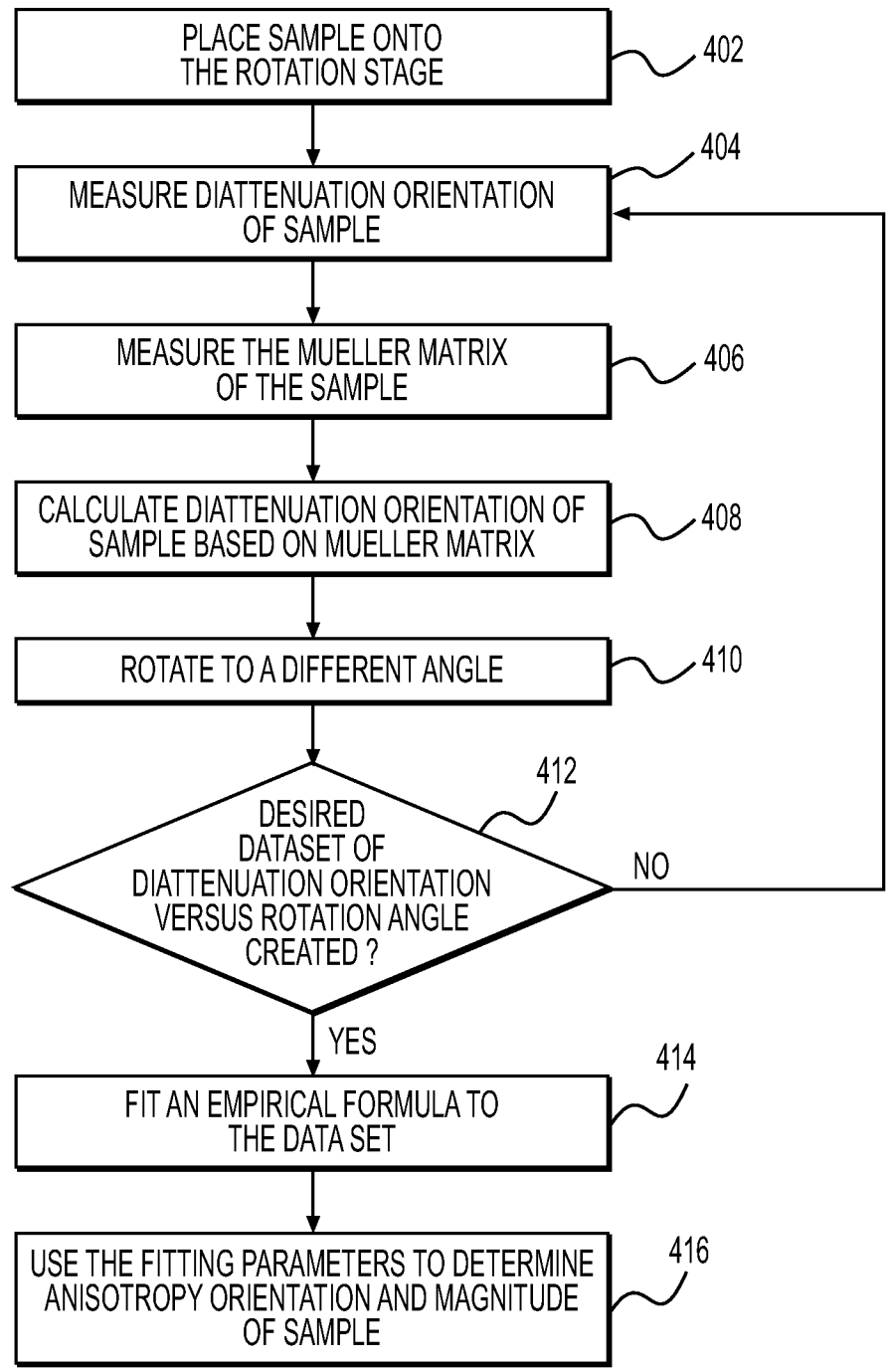
FIG. 4 depicts a flowchart an exemplary method for determining anisotropic properties of a material, such as anisotropic magnitude and anisotropic orientation, in accordance with the present invention.

FIG. 4 depicts a flowchart an exemplary method for determining anisotropic properties of a material, such as anisotropic magnitude and anisotropic orientation, in accordance with the present invention. First, an anisotropic sample 110 is placed onto the rotation stage 112 of the measurement system (step 402). Next, the Mueller matrix polarimeter measures the diattenuation orientation of the sample, in either reflection or transmission (step 404). One means for measuring diattenuation orientation is to measure the Mueller matrix using the technique described in M. H. Smith, "Optimization of a dual-rotating-retarder Mueller matrix polarimeter," Applied Optics 41(13), 2488-2493 (2002) (step 406), and then calculating the diattenuation orientation based on the measured Mueller matrix using the technique described in S. Y. Lu, et. al., "Interpretation of Mueller matrices based on polar decomposition," J. Opt. Soc. Am. A 13(5), 1106-1113 (1996), which is incorporated by reference herein (step 408).

Next, the sample is rotated to a different angle (step 410), and another diattenuation orientation measurement of the sample 110 is performed. These rotation and measurement steps are repeated to create a dataset of diattenuation orientation verses rotation angle (steps 404-412). For example, the sample 110 is rotated through an entire 360 degree rotation in 20 degree increments, measuring the diattenuation orientation at each increment. The increment angle depends on the measurement speed and measurement precision required. Using a small increment will generally improve the measurement accuracy, however, it will also increase the amount of time required for the measurement. If the desired dataset of diattenuation orientation and rotation angle is complete (step 412), the process of rotating and measuring the Mueller matrix and calculating the diattenuation orientation may stop.

The next step is to fit an empirical formula, such as the Formula 1 described above, to the data set (step 414). In this case, θ is the rotation angle at each of the measured increments, P is the measured diattenuation orientation, and the parameters A, B, $\varphi_B$, C, and $\varphi_C$ are the fitting parameters. Given the various known data for P's and θ's, any suitable nonlinear curve-fitting technique could be used to find values of the fitting parameters A, B, $\varphi_B$, C, and $\varphi_C$ that cause the Formula 1 to best match the diattenuation orientation versus rotation angle dataset measured in steps 404-412. These curve-fitting techniques are well-known to those skilled in the art.

Finally, the fitting parameters B and $\varphi_B$ determined in step 414 are used to determine anisotropy orientation and relative anisotropy magnitude of the sample (step 416). In the example of Formula 1, B is proportional to the anisotropic magnitude, and $\varphi_B$ is the anisotropy orientation. As anisotropic magnitude of the sample increases, B increases, and as the anisotropic magnitude of the sample decreases, B decreases. If the anisotropic magnitude of the sample is zero, B is zero. An LCD panel manufacturer would experimentally determine the relationship between B and the true anisotropy of the sample for a particular LCD design, and then use the measured value of B as an indicator of whether the anisotropy of panels being manufactured is too high, too low, or within their acceptable design range. The manufacturer would adjust their manufacturing process based on this feedback.

One exemplary apparatus only measures at a rotation angle that is 45° away from the nominal anisotropy orientation. This system would be able to measure the relative anisotropy magnitude, but not the anisotropy orientation.

The foregoing description of various embodiments provides illustration and description, but is not intended to be exhaustive or to limit the invention to the precise form disclosed. Modifications and variations are possible in light of the above teachings or may be acquired from practice in accordance with the present invention. It is to be understood that the invention is intended to cover various modifications and equivalent arrangements included within the spirit and scope of the appended claims.

What is claimed is:

1. A method in an apparatus for measuring optical anisotropic properties of a material, comprising:
   measuring a Mueller matrix of the material at a first angle;
   determining the diattenuation orientation of the material based on the measured Mueller matrix at the first angle;
   rotating the material to a second angle;
   measuring a Mueller matrix of the material at the second angle;
   determining the diattenuation orientation of the material based on the measured Mueller matrix at the second angle;
   storing a data set of the determined diattenuation orientations and the first and second angles;
   curve fitting a formula to the stored data set of determined diattenuation orientations and the first and second angles to determine fitting parameters, wherein the formula is:

$P=A+B \sin(2\theta+\varphi_B)+C \sin(\theta+\varphi_C)$ and wherein P is the diattenuation orientation,
   $\theta$ is a rotational angle of the material,
   B is proportional to the anisotropic magnitude of the material, and
   $\varphi_B$ is the anisotropy orientation of the material; and
   determining anisotropic orientation and a value proportional to anisotropic magnitude of the material using the determined fitting parameters; and
   repeatedly performing;
   (1) rotating the material to a different angle,
   (2) measuring a Mueller matrix of the material at the different angle, and
   (3) determining the diattenuation orientation of the material based on the measured Mueller matrix at the different angle.

2. The method of claim 1, wherein C is proportional to one of:
   1) the pre-tilt of the material and (2) a tilt error in measurement, and $\varphi_C$ is proportional to the direction of a tilt error in measurement.

3. The method of claim 2, further comprising:
   curve fitting the formula to the stored data set of determined diattenuation orientations and the first, second and different angles to determine fitting parameters; and
   determining anisotropic orientation and a value proportional to the anisotropic magnitude of the material using the determined fitting parameters.

4. The method of claim 2, further comprising:
   rotating the material through 360 degrees in 20 degree increments;
   measuring a Mueller matrix of the material at each incremented angle of the 20 degree increments; and
   determining the diattenuation orientation of the material based on the measured Mueller matrix at each angle of the 20 degree increments.

5. An apparatus for measuring optical anisotropic properties of a material, comprising:
   a polarimeter configured to:
     measure a Mueller matrix of the material at a first angle;
     measure a Mueller matrix of the material at the second angle; and
     repeatedly measure a Mueller matrix of the material at the different angle;
   a rotating fixture configured to:
     rotate the material to a second angle; and
     repeatedly rotate the material to a different angle;
   a processor configured to:
     determine the diattenuation orientation of the material based on the measured Mueller matrix at the first angle;
     determine the diattenuation orientation of the material based on the measured Mueller matrix at the second angle;
     store a data set of the determined diattenuation orientations and the first and second angles;
     curve fit a formula to the stored data set of determined diattenuation orientations and the first and second angles to determine fitting parameters, wherein the formula is:

$P=A+B \sin(2\theta+\varphi_B)+C \sin(\theta+\varphi_C)$ and wherein P is the diattenuation orientation,
     $\theta$ is a rotational angle of the material,
     B is proportional to the anisotropic magnitude of the material, and
     $\varphi_B$ is the anisotropy orientation of the material;
     determine anisotropic orientation and a value proportional to anisotropic magnitude of the material using the determined fitting parameters; and
     repeatedly determine the diattenuation orientation of the material based on the measured Mueller matrix at the different angle.

6. The apparatus of claim 5, wherein:
   C is proportional to one of: (1) the pre-tilt of the material and (2) a tilt error in measurement, and
   $\varphi_C$ is proportional to the direction of a tilt error in measurement.

7. The apparatus of claim 6, wherein the processor is further configured to:
   curve fit the formula to the stored data set of determined diattenuation orientations and the first, second and different angles to determine fitting parameters; and
   determine anisotropic orientation and a value proportional to anisotropic magnitude of the material using the determined fitting parameters.

8. The apparatus of claim 6, further comprising:
   rotating the material through 360 degrees in 20 degree increments;
   measuring a Mueller matrix of the material at each incremented angle of the 20 degree increments; and
   determining the diattenuation orientation of the material based on the measured Mueller matrix at each angle of the 20 degree increments.

* * * * *